United States Patent
Klofta et al.

(10) Patent No.: US 6,772,708 B2
(45) Date of Patent: Aug. 10, 2004

(54) WETNESS INDICATOR HAVING IMPROVED COLORANT RETENTION

(75) Inventors: Thomas James Klofta, Cincinnati, OH (US); Brandon Ellis Wise, Cincinnati, OH (US); Donald Carroll Roe, West Chester, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 10/078,137

(22) Filed: Feb. 19, 2002

(65) Prior Publication Data

US 2003/0164136 A1 Sep. 4, 2003

Related U.S. Application Data

(63) Continuation of application No. 10/015,818, filed on Oct. 30, 2001, now Pat. No. 6,655,781.

(51) Int. Cl.[7] .............................................. G01D 21/00

(52) U.S. Cl. ...................... 116/206; 116/200; 252/194

(58) Field of Search .......................... 116/206; 252/194; 604/361, 385.01, 362; 422/106, 110, 49

(56) References Cited

U.S. PATENT DOCUMENTS

| | | | |
|---|---|---|---|
| 2,681,032 A | | 6/1954 | Shaw |
| 3,607,782 A | * | 9/1971 | Rosen ........................ 116/206 |
| 3,675,654 A | | 7/1972 | Baker et al. |
| 3,702,610 A | | 11/1972 | Sheppard et al. |
| 3,731,685 A | * | 5/1973 | Eidus ......................... 116/206 |
| 3,759,261 A | | 9/1973 | Wang |
| 3,918,454 A | | 11/1975 | Korodi et al. |
| 3,952,746 A | * | 4/1976 | Summers .................... 116/206 |
| 4,022,211 A | | 5/1977 | Timmons et al. |
| 4,028,876 A | * | 6/1977 | Delatorre ................... 116/206 |
| 4,192,311 A | | 3/1980 | Felfoldi |
| 4,231,370 A | | 11/1980 | Mroz et al. |
| 4,287,153 A | | 9/1981 | Towsend |
| 4,327,731 A | * | 5/1982 | Powell ........................ 604/361 |
| 4,507,121 A | | 3/1985 | Leung |
| 4,681,576 A | | 7/1987 | Colon et al. |
| 4,705,513 A | | 11/1987 | Sheldon et al. |
| 4,735,622 A | | 4/1988 | Acuff et al. |
| 4,738,674 A | | 4/1988 | Todd et al. |
| 4,743,238 A | | 5/1988 | Colon et al. |
| 4,834,733 A | | 5/1989 | Huntoon et al. |
| 4,895,567 A | | 1/1990 | Colon et al. |
| 4,931,051 A | | 6/1990 | Castello |
| 5,035,691 A | | 7/1991 | Zimmel et al. |
| 5,066,711 A | | 11/1991 | Colon et al. |
| 5,078,708 A | | 1/1992 | Haque |
| 5,089,548 A | | 2/1992 | Zimmel et al. |
| 5,167,652 A | | 12/1992 | Mueller |

(List continued on next page.)

FOREIGN PATENT DOCUMENTS

| | | |
|---|---|---|
| EP | 0 203 715 A2 | 12/1986 |
| EP | 0 776 645 A1 | 6/1997 |
| EP | 0 925 769 A2 | 6/1999 |
| EP | 1 034 758 A1 | 9/2000 |
| EP | 1 023 024 B1 | 4/2002 |
| WO | WO 95/00099 A1 | 1/1995 |
| WO | WO 98/04225 A1 | 2/1998 |

(List continued on next page.)

Primary Examiner—Christopher W. Fulton
Assistant Examiner—Amanda J Hoolahan
(74) Attorney, Agent, or Firm—Michael P. Hayden; Jay A. Krebs; Ken K. Patel

(57) ABSTRACT

A wetness indicating composition comprising a colorant disposed in a carrier matrix. The colorant provides a visible signal when activated by urine. The colorant resists leaching from the carrier matrix by being chemically bound to a component of the carrier matrix. The colorant may be bound by ionic or covalent bonds, or by intermolecular forces. The colorant may be a pH indicator. The wetness indicating composition may be incorporated into a wearable article, such as a disposable absorbent article.

20 Claims, 6 Drawing Sheets

U.S. PATENT DOCUMENTS

| | | |
|---|---|---|
| 5,183,742 A | 2/1993 | Omoto et al. |
| 5,197,958 A | 3/1993 | Howell |
| 5,342,861 A | 8/1994 | Raykovitz |
| 5,354,289 A | 10/1994 | Mitchell et al. |
| H1376 H | 11/1994 | Osborn, III et al. |
| 5,389,093 A | 2/1995 | Howell |
| 5,435,010 A * | 7/1995 | May .......................... 116/206 |
| 5,468,236 A | 11/1995 | Everhart et al. |
| 5,647,863 A | 7/1997 | Hammons et al. |
| 5,766,212 A | 6/1998 | Jitoe et al. |
| 5,834,099 A | 11/1998 | Steinhardt et al. |
| 5,902,296 A | 5/1999 | Fluyeras |
| 5,902,669 A | 5/1999 | Steinhardt et al. |
| 5,947,943 A | 9/1999 | Lee |
| 6,066,774 A | 5/2000 | Roe |
| 6,075,178 A | 6/2000 | La Wilhelm et al. |
| 6,090,855 A * | 7/2000 | Walker ....................... 252/194 |
| 6,194,079 B1 * | 2/2001 | Hekal .......................... 252/194 |
| 6,297,424 B1 | 10/2001 | Olson et al. |
| 6,320,096 B1 * | 11/2001 | Inoue et al. ................. 604/378 |
| 6,464,635 B1 * | 10/2002 | Jimenez Cerrato et al. . 600/362 |
| 6,515,194 B2 * | 2/2003 | Neading et al. ............ 604/361 |
| 2003/0073966 A1 * | 4/2003 | Sosalla et al. .............. 604/361 |

FOREIGN PATENT DOCUMENTS

| | | |
|---|---|---|
| WO | WO 99/02985 A1 | 1/1999 |
| WO | WO 99/20216 | 4/1999 |
| WO | WO 99/56690 A1 | 11/1999 |
| WO | WO 00/00233 A1 | 1/2000 |
| WO | WO 00/15169 A1 | 3/2000 |
| WO | WO 00/76438 A2 | 12/2000 |
| WO | WO 00/76439 A2 | 12/2000 |
| WO | WO 00/76442 A1 | 12/2000 |
| WO | WO 00/76443 A1 | 12/2000 |

* cited by examiner

US 6,772,708 B2

WETNESS INDICATOR HAVING IMPROVED COLORANT RETENTION

This is a continuation of application Ser. No. 10/015,618 filed on Oct. 30, 2001, now U.S. Pat. No. 6,655,781, which is hereby incorporated by reference herein.

FIELD OF THE INVENTION

This invention is directed to a wetness indicating composition having improved colorant retention and to wearable articles comprising this wetness indicating composition.

BACKGROUND OF THE INVENTION

Wearable and absorbent articles such as diapers are well known in the art. Absorbent articles typically have an absorbent core, which is held or positioned against the body of the wearer during use by a fastening system, such that the article catches the bodily exudates. Typical absorbent articles include a topsheet facing the wearer, which permits fluid exudates to pass through, and a backsheet, which prevents the exudates from escaping from the absorbent article.

Many advances have been made in the art since the introduction of the disposable absorbent article including the introduction of wetness indicating compositions associated with the inside surface of the outer cover of the article. These compositions comprise a colorant adapted to change in appearance, i.e., appear, disappear, change color, etc., upon contact with urine in the article. However, these compositions typically do not sufficiently retain the colorant within the composition, resulting in leaching of the colorant from the composition and into portions of the wearable article or onto the wearer. Certain attempts have been made in the art to retain the colorant, such as incorporating the colorant into adhesive compositions having high melting temperatures. However, the prior art fails to provide urine-indicating compositions having sufficient colorant retention performance. Thus, it would be desirable to provide wetness indicating compositions having minimal or zero leaching of the colorant from the carrier matrix. It would also be desirable to provide absorbent articles comprising these urine-indicating compositions.

SUMMARY OF THE INVENTION

The present invention is directed to a wetness indicating composition comprising a colorant disposed in a carrier matrix. The colorant provides a visible signal when activated by urine. The colorant resists leaching from the carrier matrix by being chemically bound or by being bound by intermolecular forces to a component of the carrier matrix.

DETAILED DESCRIPTION OF THE INVENTION

The present invention is directed to a wetness indicator that may, for example, be used in conjunction with a wearable article, including but not limited to disposable absorbent articles. As used herein, the term "wearable article" refers to articles adapted to be applied or affixed to, or otherwise associated with a portion of a wearer's anatomy for a certain period of time, and often during a wearer's normal activities. Wearable articles may encircle or at least partially enclose a portion of a wearer's body, such as in the case of belts, diapers, training pants, underwear, and the like. Such wearable articles may include elasticically extensible and/or fastening components to ensure a proper fit to the wearer and/or fastening components to provide for convenient application and removal of the article from the wearer by a caregiver. Alternatively, in addition to the above-described features, at least a portion of the wearable article may be adhesively affixed to the skin of the wearer. In some embodiments, the wearable article may include a separate element, such as an insert, affixed to or associated with the wearable article. Alternatively, the wearable article may comprise an insert adapted to be attached to or associated with a durable or semi-durable article of clothing, such as underwear or a diaper cover. Although not limited to such embodiments, the present invention will generally be described below as associated with a disposable absorbent article.

As used herein, the term "absorbent article" refers to devices, which absorb and contain body exudates and, more specifically, refers to devices that are placed against or in proximity to the body of the wearer to absorb and contain the various exudates discharged from the body. The term "disposable" is used herein to describe absorbent articles that generally are not intended to be laundered or otherwise restored or reused as absorbent articles, i.e., they are intended to be discarded after a single use and, preferably, to be recycled, composted or otherwise discarded in an environmentally compatible manner. A "unitary" absorbent article refers to absorbent articles which are formed of separate parts united together to form a coordinated entity so that they do not require separate manipulative parts like a separate holder and/or liner. A preferred absorbent article embodiment of the present invention is the unitary disposable absorbent article, diaper 20, shown in FIG. 1. As used herein, the term "diaper" refers to an absorbent article generally worn by infants and incontinent persons about the lower torso. The present invention is also applicable to other wearable and absorbent articles such as incontinence briefs, incontinence undergarments, absorbent inserts, diaper holders and liners, feminine hygiene garments, bandages and the like.

Figure 1:
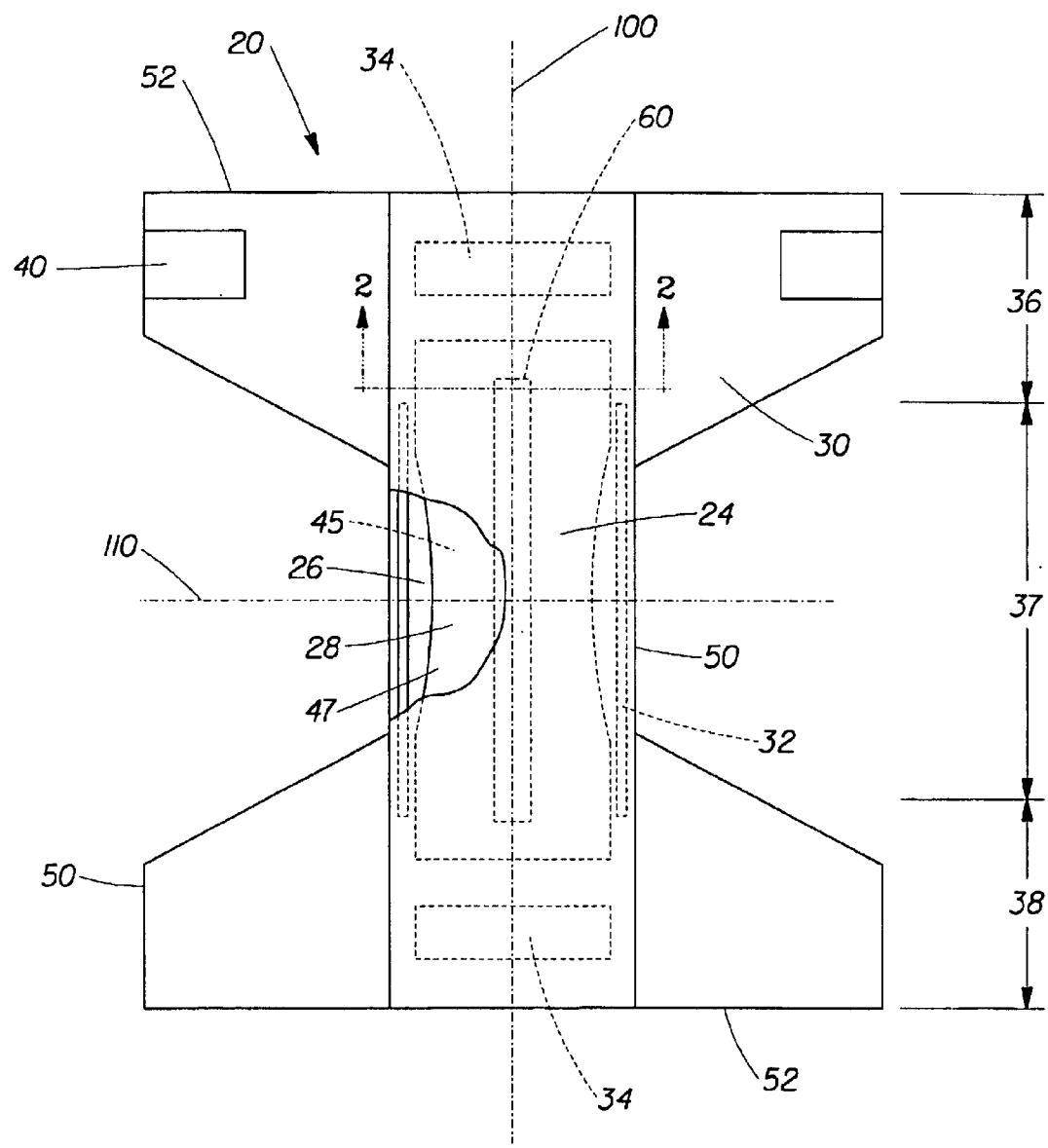
FIG. 1 shows a plan view of a disposable diaper embodiment of the present invention.
Figure 2:
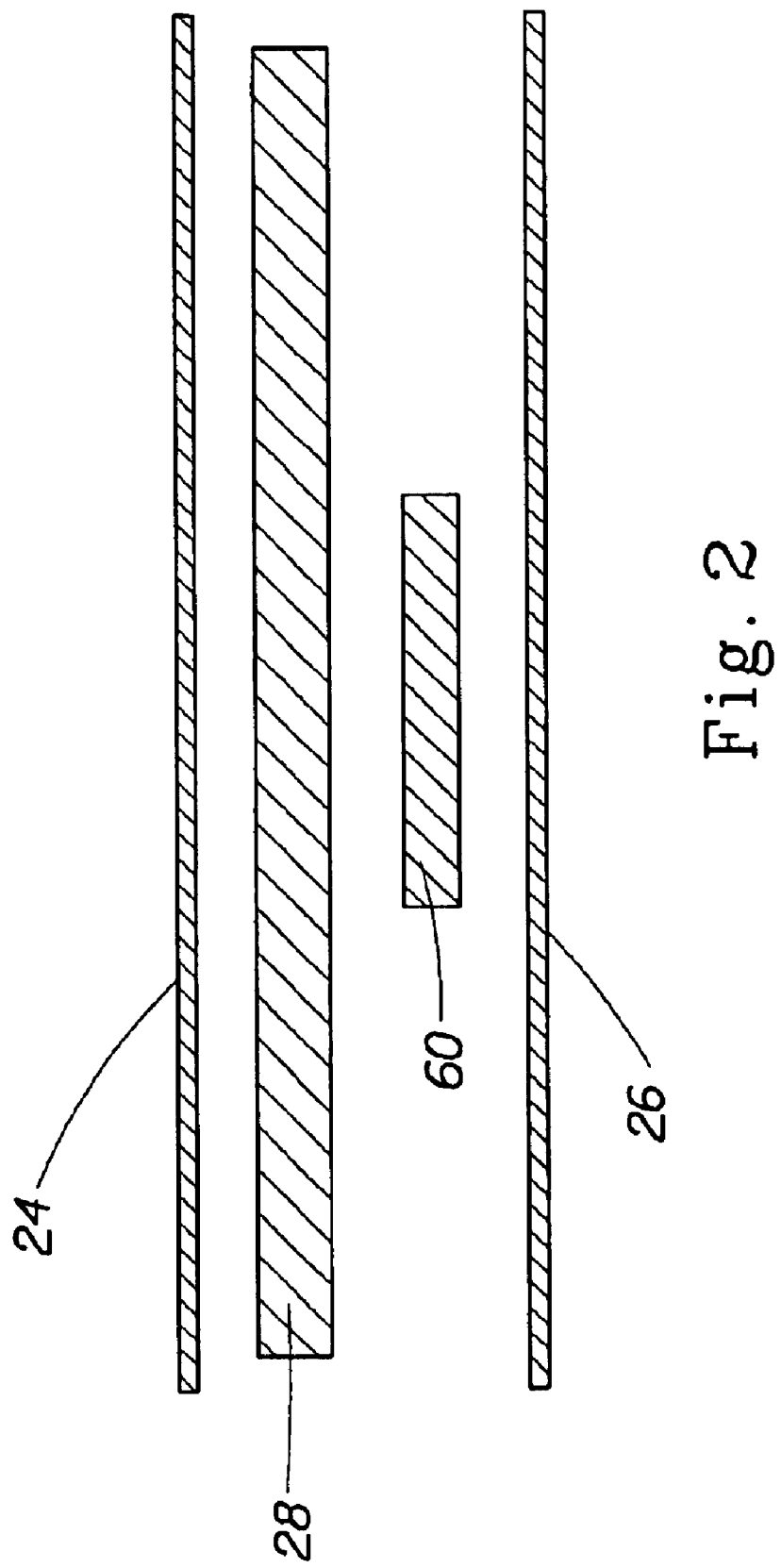
FIG. 2 shows a section view of a portion of the disposable diaper of FIG. 1.
Figure 3:
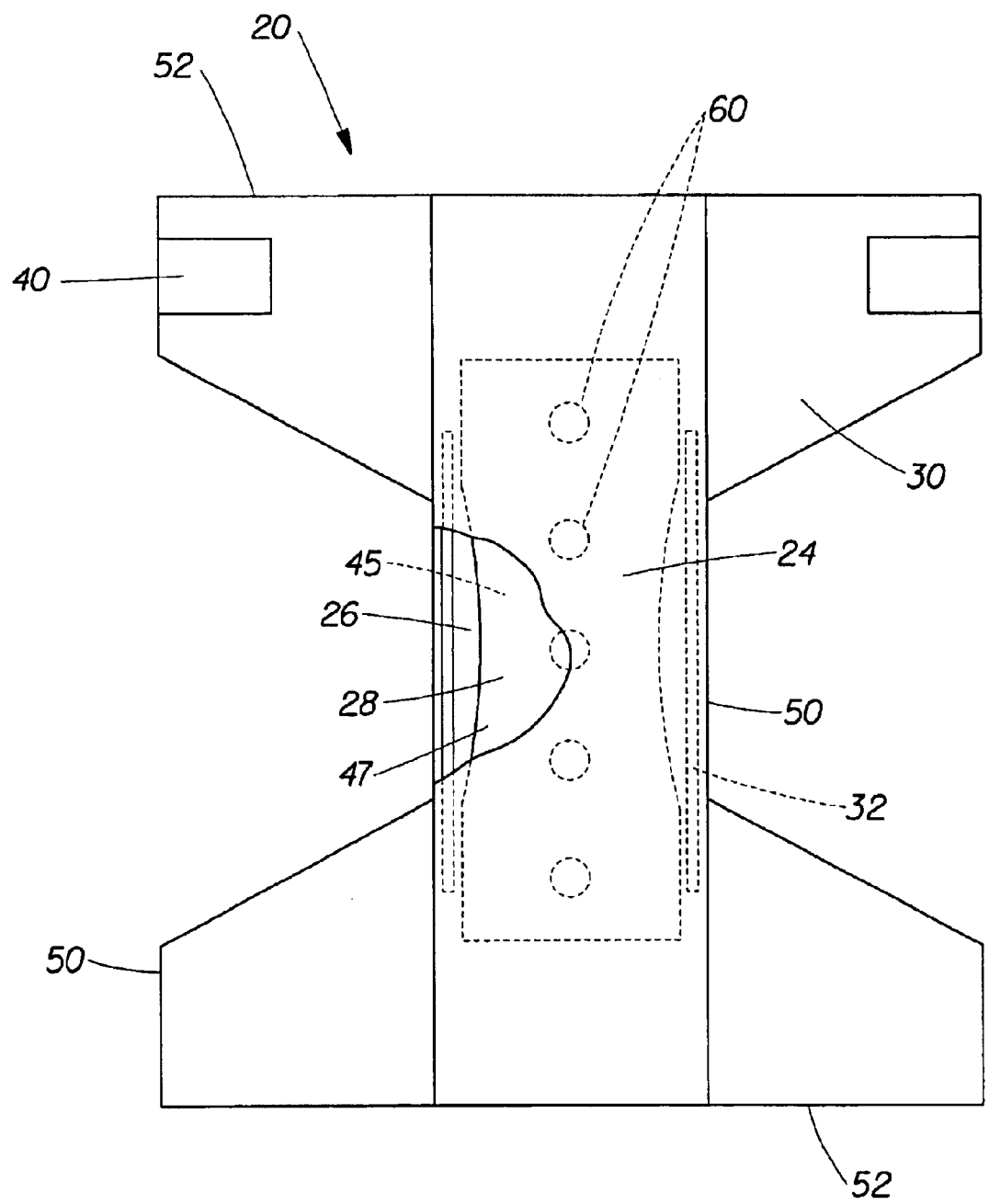
FIG. 3 shows a plan view of an alternative disposable diaper embodiment of the present invention.
Figure 4:
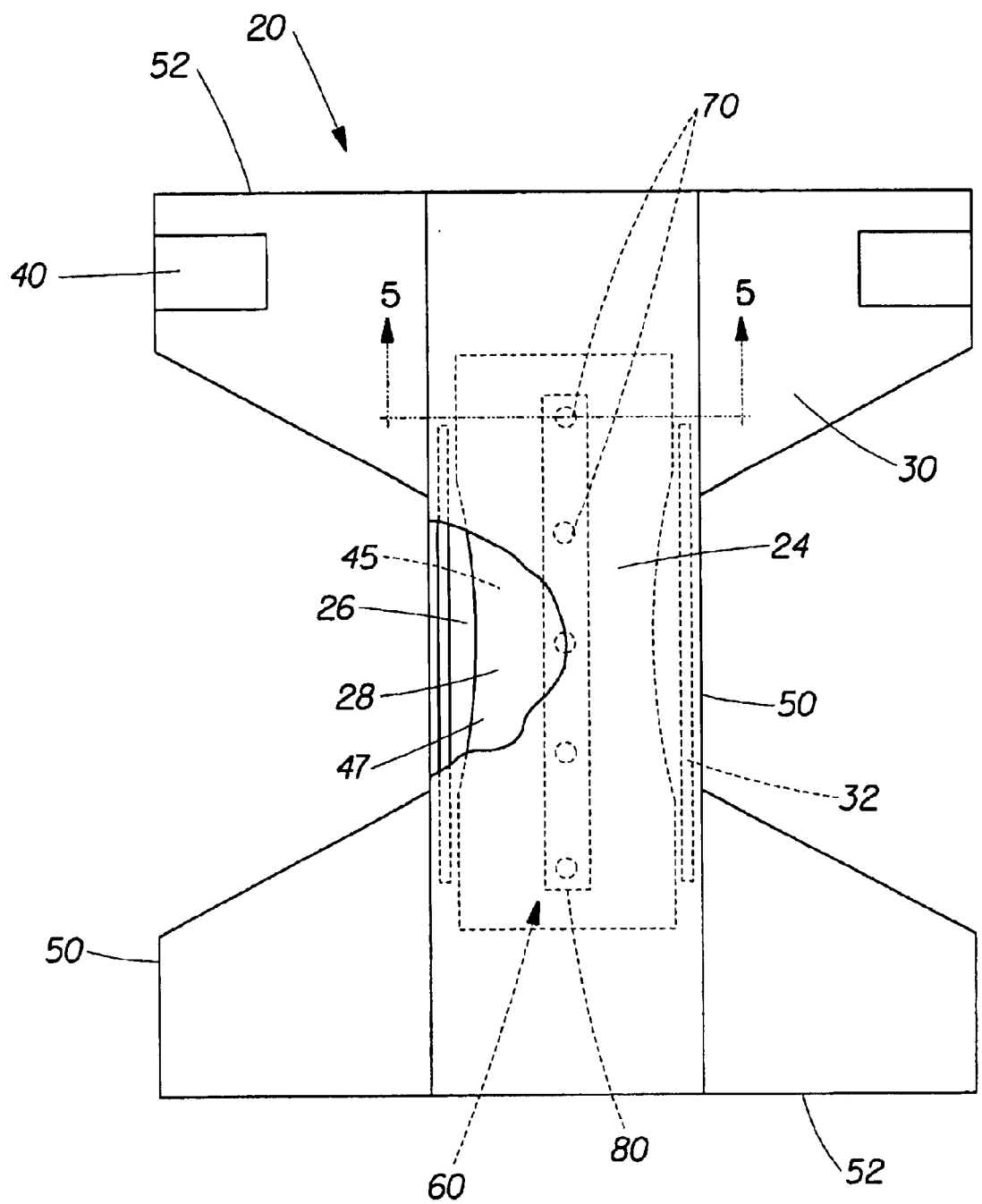
FIG. 4 shows a plan view of another alternative disposable diaper embodiment of the present invention.
Figure 5:
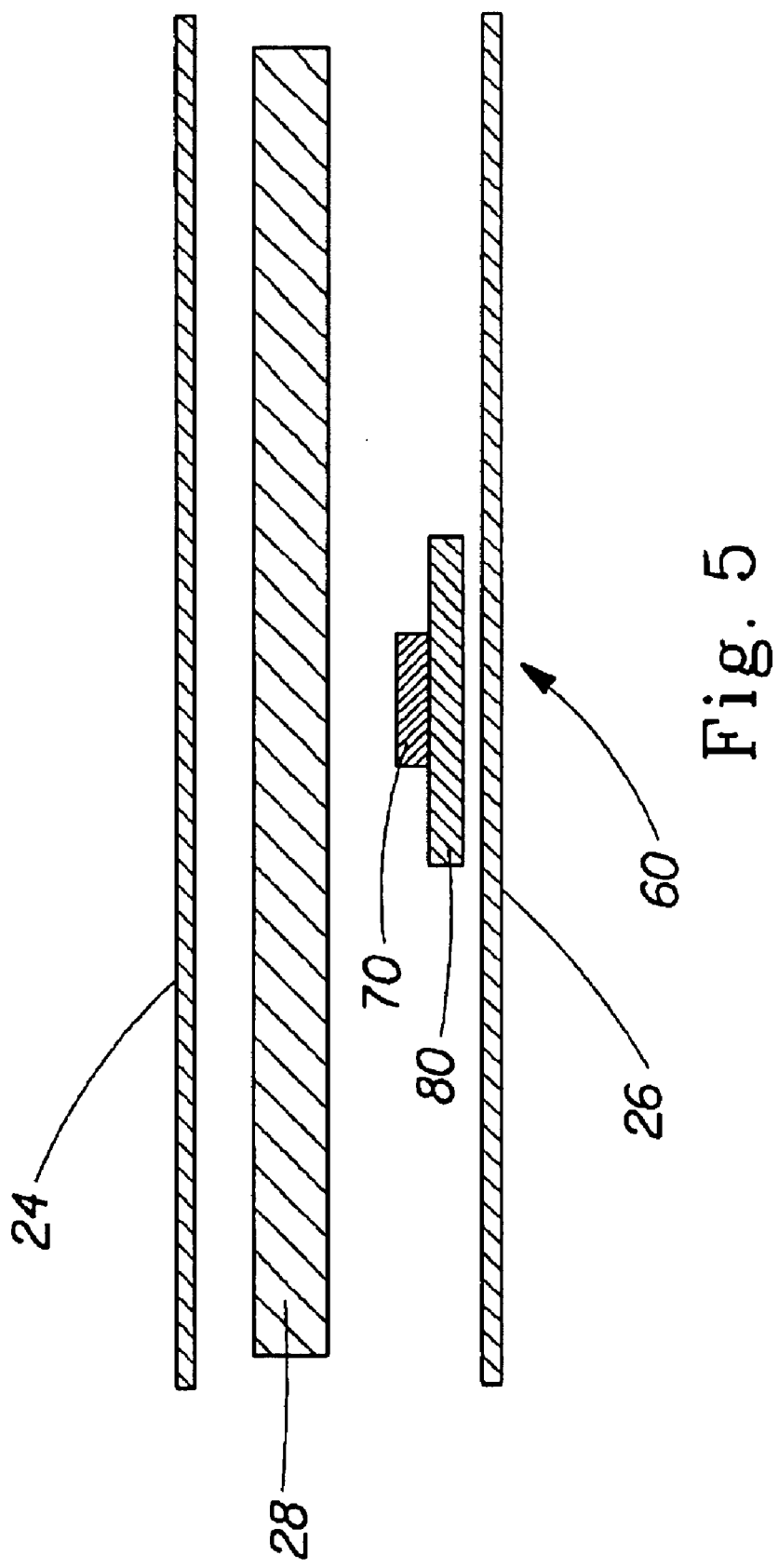
FIG. 5 shows a section view of a portion of the disposable diaper of FIG. 4.

FIG. 1 is a plan view of the diaper 20 of the present invention in a flat-out, state with portions of the structure being cut-away to more clearly show the construction of the diaper 20. The portion of the diaper 20, which faces the wearer, is oriented towards the viewer. As shown in FIG. 1, the diaper 20 preferably comprises a liquid pervious topsheet 24; a liquid impervious backsheet 26; an absorbent core 28 that is preferably positioned between at least a portion of the topsheet 24 and the backsheet 26; side panels 30; elasticized leg cuffs 32; an elastic waist feature 34; and a fastening system generally designated 40. The diaper 20 is shown in FIG. 1 to have a first waist region 36, a second waist region 38 opposed to the first waist region 36 and a crotch region 37 located between the first waist region 36 and the second waist region 38. The periphery of the diaper 20 is defined by the outer edges of the diaper 20 in which longitudinal edges 50 run generally parallel to the longitudinal centerline 100 of the diaper 20 and end edges 52 run between the longitudinal edges 50 generally parallel to the lateral centerline 110 of the diaper 20.

While the topsheet 24, the backsheet 26, and the absorbent core 26 may be assembled in a variety of well-known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The backsheet 26 is generally that portion of the diaper 20 positioned adjacent garment facing surface 45 of the absorbent core 28 that prevents the exudates absorbed and contained therein from soiling articles that may contact the diaper 20, such as bedsheets and undergarments. The topsheet 24 is preferably positioned adjacent body facing surface 47 of the absorbent core 28 and may be joined thereto and/or to the backsheet 26 by any attachment means known in the art. As used herein, the term "joined" encompasses configurations whereby an element is directly secured to another element by affixing the element directly to the other element, and configurations whereby an element is indirectly secured to another element by affixing the element to intermediate member(s) that in turn are affixed to the other element. The topsheet 24 is preferably compliant, soft-feeling, and non-irritating to the wearer's skin. Further, at least a portion of the topsheet 24 is liquid pervious, permitting liquids to readily penetrate through its thickness.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

As noted above, the diaper 20 may also include a fastening system 40. The fastening system 40 preferably maintains the first waist region 36 and the second waist region 38 in a configuration so as to provide lateral tensions about the circumference of the diaper 20 to hold the diaper 20 on the wearer. The fastening system 40 preferably comprises a surface fastener such as tape tabs, hook and loop fastening components and/or hermaphroditic fastening components, although any other known fastening means are generally acceptable. In alternative embodiments, opposing sides of the article may be seamed or welded to form a pant. This allows the article to be used as a pull-on type diaper, such as a training pant.

Caregivers frequently desire to know whether urine is present in an absorbent article, such as a diaper, and/or how much urine is present. This may be due to health concerns, e.g., whether the child is getting enough fluid, or skin health/containment concerns, e.g., whether the diaper contains sufficient urine to warrant changing. The presence of urine may be signaled to the caregiver as a color or contrast change detectable in at least a portion of the article and visible prior to removal of the article, e.g., through the outer cover of the article, by a wetness indicator, which is termed a "urine indicator" in this usage. Colorants, such as food grade dyes and pH indicators that change color when wetted with urine, may be used in this context. The art describes a number of urine or wetness indicator approaches employing these types of colorants, including their incorporation into the absorbent core or application to, or association with, the inside surface of the backsheet. One common approach, including a material used in currently marketed PAMPERS™ diapers in Japan, is to formulate a hot melt adhesive containing a small quantity of a pH indicator. These materials are known as hot melt wetness indicators (HMWI).

The primary issue with HMWIs and the other colorant based wetness indicators described in the art is the tendency of the colorant to leach from the carrier matrix. A carrier matrix is a quantity of a material or materials serving to hold or retain the wetness indicator in the desired position within the product, such that urine will come into contact with it and such that a physical change in the wetness indicator, such as a change in color, will be sensible to the wearer or a caregiver. In certain embodiments of the present invention, components of the carrier matrix can also contribute to reduced leaching of the colorant due to the formation of intermolecular binding forces. Excess urine may cause the colorant to diffuse out of, i.e., leach from, the carrier matrix and migrate toward and possibly through the backsheet and/or topsheet. This may lead to consumer negatives such as clothing or bedding staining, and/or may cause the wetness indicator to appear unsightly through the backsheet, i.e., the applied pattern of the wetness indicator composition may become blurry, indistinct, or otherwise aesthetically displeasing. Wetness indicators resistant to leaching of the colorant from the matrix are highly desirable; therefore, to minimize concerns related to colorant migration within, or out of, the article.

Preferred wetness indicating compositions are highly resistant to colorant leaching, as described above, and are resistant to premature activation in high humidity environments, which may render the wetness indicator less effective in detecting and/or indicating the presence of urine in a wearable article. For instance, exposure to a high level of humidity may partially activate wetness indicating compositions that are not highly resistant to colorant leaching and thereby make any color change in the presence of urine less noticeable. Additionally, preferred wetness indicating compositions should have excellent signal clarity and kinetics, i.e., the signal should be visible soon after contact with urine.

The wetness indicators of the present invention generally comprise at least one colorant disposed in a carrier matrix.

The colorant is activatable by urine, i.e., the colorant may change in color, appear, disappear, or change in intensity or visual distinctiveness in response to contact with urine or a component thereof. The carrier matrix comprises one or more components that may facilitate the incorporation of the wetness indicator composition into a finished product, such as a wearable article, and/or retain the colorant during initial placement or during use. Upon contact with urine, the carrier matrix preferably allows sufficient urine to contact the colorant and effect a change in appearance while preventing the colorant, in either its virgin or activated state, from leaching out of the carrier matrix into the surrounding environment, such as the absorbent core of a wearable article. The wetness indicator of the present invention may be incorporated into the article in any desired pattern or configuration, including, but not limited to, stripes, dots, geometric shapes, alphanumeric characters, pictorial representations of animate or inanimate objects, or any combination or arrangement thereof.

Urine contacting the wetness indicator at least partially diffuses into the carrier matrix where it contacts the colorant. If the colorant is a pH indicator, contact with urine having a higher pH than the indicator threshold results in a color change, e.g., yellow to blue, etc. If the colorant is a food grade dye, contact with urine may solubilize the dye, enabling it to bloom within or to the surface of the carrier matrix, resulting in an intensification of the dye's color.

Some pH indicators are neutral in charge and lightly colored at acidic pH's. For example, bromocresol green, bromocresol purple, and bromophenol blue are all neutrally charged and yellow in color at an acidic pH. As the pH exceeds the $pK_a$ of the indicator, a charge and related color change occurs. For example, bromophenol blue changes from a yellow neutral state to an anionic blue state at a pH greater than its $pK_a$ of approximately 4.0.

In these embodiments, the pH indicator is incorporated into the carrier matrix in its neutral acid form. The neutral charge of the pH indicator allows it to be more easily solubilized into hydrophobic systems. Upon contact with urine, which typically has a pH in the range of 5.5 to 8.0, the indicator changes color, e.g., from yellow to blue. In addition to the color change, the charge on the pH indicators also changes from neutral to anionic at pH values above its pKa value. This negative charge on the pH indicator not only causes the dye molecule to change color, but the more polar nature of the anion also enhances the solubility and leaching of the dye into an aqueous environment.

In certain embodiments of the present invention, incorporating the colorant, i.e., indicator or dye, into a hydrophobic matrix that preferentially "locks" the molecule into the matrix may inhibit the leaching of the anionic colorant into the urine. In these embodiments the anionic colorant may become preferentially absorbed into the matrix due to intermolecular bonding forces. Some of the types of intermolecular forces responsible for inhibiting the leaching of the colorant into the urine include hydrogen bonding, electrostatic forces, van der Waals forces and hydrophobic interactions. Thus, even though the charged portion of the colorant in its virgin state would be hydrated by water in the urine, leaching of the colorant may be inhibited due to intermolecular bonding forces between the materials of the matrix and the colorant.

However, in preferred embodiments of the present invention, the colorant is chemically bound to at least one component of the carrier matrix, such as a cationic species. Chemical bonds include covalent, ionic, and metallic bonds.

In embodiments wherein the carrier matrix comprises a cationic species, the cationic species may function as a leaching inhibitor to reduce or completely eliminate leaching of an anionic dye colorant from the carrier matrix. In particular, leaching of the anionic dye indicator is preferably inhibited via addition of a permanently charged cationic molecule in the wetness indicator composition. For example, quaternary ammonium compounds are particularly effective leaching inhibitors by inhibiting colorant leaching from the matrix and enhancing the contrast and clarity of the wetness indicator pattern. Without wishing to be bound by theory, we believe the cationic quaternary ammonium compound forms an ionically bonded coacervate with the negatively charged pH indicator due to the strong coulombic interaction between the anionic dye and the cationic quaternary ammonium compound. The coacervate complex formed between the anionic dye and cationic quaternary ammonium compound neutralizes the charge in both species and dramatically reduces both of their solubilities in polar solvents such as water or urine, thereby dramatically inhibiting leaching of the colorant from the carrier matrix. The intermolecular forces between the coacervate and the carrier matrix, as described above, may further limit the diffusion and mobility of the colorant into an aqueous environment such as urine.

This leaching inhibition is particularly beneficial in locking the pH indicator or dye directly within the wetness indicator on the backsheet rather than allowing free diffusion of the dye or indicator through the diaper core and possibly contaminating the diaper topsheet. In addition, a clearer and more distinct wetness indicator pattern may be produced in embodiments wherein dyes or pH indicators are locked into the matrix. As noted, dyes or pH indicators that diffuse out of the wetness indicator pattern tend to appear blurred and less distinct.

In certain embodiments of the present invention, the addition of the quaternary ammonium compound may also function to darken the color change of sulfonephthalein pH indicators, especially those belonging to the sulfonephthalein class of pH indicators. Without wishing to be bound by theory, we believe this may be attributed to several possible factors: 1) alkaline impurities within the quaternary ammonium raw material, 2) absorption shifting and absorptivity coefficient increases due to coacervate formation and, or 3) increased anionic dye formation. For example, the alkaline impurities possibly result in a more basic environment surrounding the dye. Therefore at the higher pH, greater concentrations of blue anionic dye species are formed and a darker color results. Additionally, the coacervate formed between the anionic pH indicator and the cationic quaternary ammonium compound may cause an absorption spectral shift and absorptivity coefficient increase such that the dye is more darkly colored when associated to the cationic species. Finally, the coacervate formation may cause a concomitant decrease in the anionic dye species concentration after contact with urine. This decrease in the anionic species concentration can cause a shift in the equilibrium such that more anionic dye species are formed via the Le Chatelier Principle. This higher concentration of the blue anionic dye indicator leads to a darker blue color. Of course, the darker blue color may be the result of any combination of these phenomena.

As previously described, the cationic quaternary ammonium compound is believed to reduce leaching of the anionic dye via formation of an insoluble coacervate. Alternatively, it is possible to inhibit leaching of a cationic dye or cationic pH indicator by incorporating an anionic compound into the carrier matrix of the wetness indicator. For example, many polyacrylic acid polymers and organic acids such as stearic acid are negatively charged at pH's above approximately 5. If the pH indicator undergoes a transition to a cationic species at the typical urine pH of 5.5 to 8.0, the formation of an insoluble coacervate may occur, inhibiting leaching in a manner similar to the systems described above.

The carrier matrix may comprise components that modify the relative hydrophilicity/hydrophobicity (HLB ratio), modify the melting point of the wetness indicating composition, change the flexibility of the indicating composition, enhance the adhesion to the backsheet material, affect the leaching of the colorant, and/or alter the humidity resistance of the composition. For instance, some waxes increase the flexibility and hydrophobicity of the composition while also increasing the adhesive tack to the backsheet. Some waxes also reduce the leaching of the colorant into aqueous environments due to intermolecular binding forces. Non-limiting examples of suitable natural and synthetic waxes include highly branched waxes, such as microcrystalline waxes, paraffin waxes, polyethylene waxes, polyethylene glycol type waxes, silicone waxes, beeswax, ozokerite, ceresin, and carnauba wax.

Linear primary alcohols, such as stearyl alcohol, may be added to the carrier matrix and may function as co-emulsifiers and enhance the composition stability. The carrier matrix may comprise any composition that may be applied to a substrate, i.e., a structural component of the article such as the backsheet, the topsheet, or the absorbent core of an absorbent article, in preferably a liquid form that at least partially solidifies after application to the substrate. Preferably, the solidification of the composition onto the backsheet substrate is relatively rapid to avoid potential transfer and loss of the composition to other regions of the article and/or processing equipment.

If the carrier matrix is an emulsion or solution, solidification may occur via the evaporation of a solvent such as water or other safe solvent. In preferred embodiments of the wetness indicating composition of the present invention, the carrier matrix is a meltable composition and solidifies, i.e., achieves a solid or semi-solid physical state, rapidly via cooling. In certain embodiments, the inclusion of crystalline materials such as paraffin waxes can increase the solidification rate of the composition. The carrier matrix may be an adhesive or other meltable composition having a melting point above room temperature, such as a skin care composition or a component thereof. Exemplary skin care compositions are described in U.S. Pat. Nos. 5,607,760; 5,609,587; 5,635,191; 5,643,588; 6,118,041; 6,107,537; and 5,968,025, incorporated herein by reference.

Carrier matrices may include components such as waxes, e.g., microcrystalline, paraffin, natural, synthetic, polyethylene type, polyethylene glycol type, silicone type, etc., surfactants such as ethoxylated alcohols, fatty alcohols, high molecular weight alcohols, esters, polymers, and any other natural or synthetic waxes or olefinic materials as known in the art. Optionally, the carrier matrix may also include viscosity increasing agents and/or hardening agents. Suitable examples of viscosity increasing agents include polymeric thickeners such as block copolymers having polystyrene blocks on both ends of a rubber molecule, copolymers of ethylene and vinyl acetate, hydrogenated castor oil, polymers, metal salts of fatty acids, silicas and/or derivatized silicas, organoclays such as the modified and unmodified hectorites and bentonites, modified clays such as modified laponite clays, dibenzylidene sorbitol, alkyl galactomannan, aluminum magnesium hydroxide stearate/oil blends, and lauroyl glutamic dibutylamide. Hardening agents may include the aforementioned waxes, C14–22 fatty alcohols, C23–60 alcohols, C14–22 fatty acids, C23–60 carboxylic acids, hydrogenated vegetable oils, polymers, sorbitan esters, and other high molecular weight esters.

The colorant preferably is attracted to the carrier matrix or a component thereof, and forms ionic or covalent bonds therewith, i.e., is ionically or covalently bound thereto. As previously described, the carrier matrix may comprise a cationic species capable of forming ionic bonds with anionic colorant molecules, such as activated pH indicators, thereby significantly reducing the possibility of the colorant leaching from the wetness indicator composition. Other suitable leaching inhibitor materials include cationic clay materials, such as sodium montmorillonite, that may attract and ionically bind anionic colorants, such as activated pH indicators as described herein. Other clays with known anionic binding capacity, i.e., cationic clays, include beidellite, nontronite, saponite, vermiculite, kaolinite, and clays reacted with quaternary compounds such as tetramethylammonium chloride, and polyquarternized amines.

Alternatively, the colorant may be covalently bound to at least one component of the carrier matrix. For example, the dye or pH indicator may be functionalized onto a polymer backbone such that the dye or pH indicator is covalently bound to the polymer. Specifically, the sulfonephthalein class of pH indicators may be covalently coupled to amine and hydroxyl containing materials via cyanuric chloride activation. Examples of amine containing materials that can be coupled to the sulfonephthalein indicators via cyanuric chloride include chitosan, polyethyleneimines, polyamines and polyacrylamides. The cyanuric chloride coupling reagent may also be used to couple the colorant to hydroxyl containing molecules or polymers such as cellulose and polyethylene glycols. To inhibit the solubility of the coupled complex in an aqueous liquid such as urine, hydrophobic water insoluble functionalities such as long alkyl chains may be derivatized onto the colorant or polymer backbone via any means known in the art. Other coupling reagents that may be used to covalently bind the colorant to a component of the carrier matrix include carbodiimides that can link carboxyl moieties to amine moieties, glutaraldehyde that can link amine functionalities to one another, cyanogen bromide that can link hydroxyl groups to amine moieties, and hydrazine that can link amides to aldehyde functionalities.

In certain alternate embodiments, the carrier matrix may comprise at least one component in which the colorant is substantially soluble and for which the colorant has a strong affinity. For example, the carrier matrix may include a component having an aromatic group to which the pH indicator's aromatic group has an affinity. For example, the carrier matrix may include a material having a styrene moiety, such as a styrene block copolymer, e.g., a styrene-butadiene, or SBS, copolymer, and the pH indicator may comprise bromophenol blue. Since both molecules contain aromatic ring hydrocarbons, there are intermolecular forces that can aid in inhibiting the dye leaching effect. In another example, the carrier matrix may comprise a clay material for which the colorant has an affinity. For instance, modified organoclay hectorite rheological additives contain long alkyl chains that may interact with dyes and indicators containing alkyl chains, reducing the tendency of the colorant to leach from the carrier matrix. As noted, such materials as waxes and linear primary alcohols incorporated in the carrier matrix can also reduce the leaching of the colorant through these intermolecular forces of attraction.

The carrier matrix preferably includes a surfactant to provide or enhance both composition phase stability and wettability. Surfactants comprise both polar and hydrophobic moieties. Because of this unique structure, they facilitate the stabilization of compositions containing both polar and hydrophobic ingredients. For example, surfactants employed in this invention allow for the mixing and stabilization of polar quaternary ammonium compounds with microcrystalline waxes. In addition to facilitating the mixing of dissimilar materials, the inclusion of the surfactant may also increase the speed of the color change of the pH indicator after urine contacts the composition. Since these compositions may contain relatively high concentrations of hydrophobic ingredients such as waxes and linear primary alcohols, the wettability of such a matrix with urine is often nonoptimal, preventing the pH indicator from being wetted out and changing color at a desirable rate. For this reason, surfactants are preferably added to the wetness indicating compositions of the present invention to enhance the wettability of the composition. For example, non-ionic surfactants such as ethoxylated alcohols effectively enhance the wettability of many wetness indicating compositions, allowing the color of the wetness indicator to change in less than about five minutes. Non-limiting examples of other surfactant classes that may also improve stability and wettability include anionic and cationic surfactants, alkoxylated alkylates such as PEG-20 stearate, end group-capped alkoxylated alcohols, alkoxylated glyceryl and polyglyceryl alkylates such as PEG-30 glyceryl stearate, glyceryl alkylates such as glyceryl stearate, alkoxylated hydrogenated castor oil, alkoxylated lanolin and hydrogenated lanolin, alkoxylated sorbitan alkylates, sugar derived surfactants such as the alkyl glycosides and sugar esters, poloxamers, polysorbates, and sulfo succinic acid alkyl esters.

Preferably, the concentrations and structures of each of the components within the indicating composition are preferably concurrently optimized for several important properties: 1) minimal colorant leaching, 2) high contrast color change, 3) rapid color change kinetics, 4) stability to humidity during storage, 5) adhesion to the backsheet, 6) ease of processing, and 7) low cost. As noted above, in certain preferred embodiments colorant leaching inhibition may be due predominately to the formation of the neutrally charged coacervate between a cationic species, such as a quaternary ammonium compound, and an anionic activated colorant. As described above, inclusion of a hydrophobic wax, linear primary alcohol, or aromatic containing material into the carrier matrix may aid in locking this coacervate and colorant into the matrix. In certain embodiments, the wax, linear primary alcohol, or aromatic containing material may also contribute to enhanced stability in high humidity environments.

The inclusion of acidic materials also plays an important role in stabilizing the system to premature color changes caused by exposure to humid environments. The inclusion of the acidic materials helps maintain a low pH environment around the pH indicator even when the system is exposed to high humidities. This maintenance of a low pH environment keeps the pH indicator in its neutral and lightly colored state. Acids which are particularly effective in stabilizing the wetness indicator formula to high humidities include organic acids such as monostearyl phosphate, citrate esters such as monostearyl citrate, glycolate esters, lactate esters, fatty acids such as stearic and palmitic acid, ether carboxylic acids, N-acyl sarcosinic acid surfactants, N-acyl glutamic acid surfactants, N-acyl ethylenediaminetriacidic acid surfactants, alkane sulfonic acids, alpha-olefin sulfonic acids, alpha-sulfonic acid fatty acid methyl esters, sulfate esters, fruit acids such as citric acid, salicylic acid, and inorganic acids such as phosphoric acid.

The addition of too much acid or hydrophobic materials within the carrier matrix may inhibit both the intensity of the color change and the kinetics of this change. Thus, it is important to carefully balance the amount of each of the ingredients in the formula to optimize the properties of the wetness indicator composition. As noted, another important ingredient in these formulas is the inclusion of a wetting agent. In this case, ethoxylated alcohols have been found to be particularly effective. The role of the wetting agent is to increase the speed of the color change kinetics and to enhance the stability of the fully formulated mixture. Since a material such as a hydrophobic wax and a charged quaternary ammonium compound may be incompatible, the inclusion of an ethoxylated alcohol surfactant, which possesses both hydrophobic and hydrophilic moieties, helps bridge these incompatible materials into a stable matrix. Addition of linear alcohol and carboxylic acid co-emulsifiers such as stearyl alcohol and behenyl alcohol may also function to enhance the stability and wettability of these systems.

For urine indicating compositions comprising a leaching inhibitor, such as a quaternary ammonium compound, the colorant leaching inhibition is greatest for anionic colorants due to the strong attraction between the cationic leaching inhibitor and the anionic activated colorant, as described above. The sulfonephthalein class of pH indicators are particularly preferred colorants. In an acidic state, the sulfonephthalein class of indicators have a "neutral" charge and are typically yellow in color. The neutral charge enhances the solubility of these pH indicators in relatively hydrophobic carrier matrices as described above. Upon contact with urine having a pH higher than their $pK_a$, the sulfonephthalein class of pH indicators typically change to a blue-green color and have an anionic charge, allowing the pH indicator to be scavenged by the cationic quaternary ammonium compound. Examples of suitable sulfonephthalein pH indicators include bromocresol green, bromocresol purple, m-cresol purple, cresol red, chlorophenol red, bromothymol blue, bromopyrogallol red, bromoxylenol blue, and bromophenol blue.

Other examples of pH indicators and dyes which are neutral in their acidic state and anionic after contact with urine include monoazo dyes such as acid alizarin violet N, monoazo pyrazolone dyes such as acid yellow 34, diazo dyes such as acid black 24, acid anthraquinone dyes such as acid black 48 and alizarin complexone dihydrate, amphoteric anthraquinone dyes such as acid blue 45, triphenylmethane dyes such as acid fuchsin, phthalein type dyes such as o-cresolphthalein, and xanthene dyes such as 2',7'-dichlorofluorescein and eosin B.

Alternatively, a cationic dye or cationic pH indicator may be scavenged with an anionic leaching inhibitor. Dyes and/or pH indicators that are neutral in their basic state and cationic after contact with urine include heterocyclic acridine aromatics such as acridine and acridine orange, diphenylmethane dyes such as auramine O, triphenylmethane dyes such as basic fuchsin, cationic thiazine dyes such as azure C, cationic anthraquinone dyes such as basic blue 47, and phthalocyanine type dyes such as copper phthalocyanine. Permanently charged cationic dyes and pH indicators that may be scavenged by an anionic leaching inhibitor include quaternized phthalocyanine type dyes such as alcec blue and cationic polymethine dyes such as astrazon orange G. Neutral dyes and pH indicators that may be bound to the matrix due to intermolecular forces described above include anthraquinone type such as alizarin, the neutral complex dyes such as azure A eosinate, and the terpene type such as trans-beta-carotene.

As described above, when a neutral acidic, i.e., anionic when activated, pH indicator contacts urine having a pH greater than its $pK_a$, the indicator changes color and assumes an anionic charge, i.e., the indicator is "activated." In preferred embodiments including a cationic species as a leaching inhibitor, the leaching inhibitor is preferably a cationic quaternary ammonium compound adapted to associate with the activated anionic form of a pH indicator, especially the sulfonephthalein class of pH indicators. The dialkydimethylammonium quaternary compounds are especially effective in reducing the leaching of anionic dyes or pH indicators. Suitable examples include dicocoalkyldimethlyammonium chloride, di(hydrogenated tallowalkyl) dimethlyammonium chloride, and distearyldimethylammonium chloride. An especially preferred cationic quaternary ammonium compound is 2-ethylhexylhydrogenatedtallowalkyldimethlyammonium methyl sulfate. Alkyltrimethylammonium chlorides may also in some embodiments, function as leaching inhibitors. Examples include dodecyltrimethylammonium chloride, hexadecyltrimethylammonium methylsulfate, and octadecyltrimethylammonium chloride. Other classes of cationic quaternary ammonium salts that may act as leaching inhibitors include the imidazoline quaternary class, the mono-, di-, tri- and tetra- amidoamine quaternary class, the mono-, di-, tri- and tetra-alkyl quaternary class, the mono-, di-, tri- and tetra-benzyl quaternary class, the benzylalkyl quaternary class of cationic compounds, the cationic diquaternary class, and the cationic ethoxylated quaternary class. Finally, it should be noted that the counter anion used in neutralization of the cationic quaternary compound is not specifically limited to chloride. Other anions can also be employed and non-limiting examples include methyl sulfate and nitrite.

Other cationic materials that would likely be useful aids in the inhibition of leaching include amine acid salts, polyacryamidopropyltrimmonium chloride, PEG-2 dimeadowfoamamidoethylmonium methosulfate, meadowfoam glyceryl quaternium, alkyl betaines, alkyl amido betaines, imidazolinium betaines, sulfobetaines, quaternized poly (vinylpyridine), amidoamine acid salts, poly(imine) acid -salts, polyethylene imine acid salts, cationic polyacryamides, poly(vinylamine) acid salts, cationic ionene polymers, poly(vinylbenzyl onium salts), poly (vinylimidazolinium salts), quaternized silicone compounds such as the diquaternary polydimethylsiloxanes, poly(vinyl alcohol) quaternary materials, cationic guars, polydimethyldiallylammonium chloride, cationic and anionic exchange resins and polymers, copolymers of vinylpyrrolidone and methyacrylamidopropyltrimethylammonium chloride, acidified polyvinylpyrrolidones, acidified polyvinylpolypyrrolidones, acidified copolymers of vinylpyrrolidone and vinylacetate, acidified copolymers of vinylpyrrolidone and dimethylaminoethylmetacrylate, copolymers of vinylpyrrolidone and methacrylamidopropyl trimethylammonium chloride, copolymers of quaternized vinylpyrrolidone and dimethylaminoethylmethacrylate, acidified vinylcaprolactam based polymers, acidified copolymers of vinylpyrrolidone and styrene, acidified copolymers of vinylpyrrolidone and acrylic acid, cationic polyelectrolyte polymers, and acidified n-alkyl-2-pyrrolidones.

It should be noted that the amines previously mentioned can be rendered cationic via several different approaches. One means of converting the amine into a cationically charged species is via contact with the urine itself since amines are protonated at the typical urine pH range of 5.5 to 8.0. In addition, the acid salt of the amine can be prepared prior to formulating into the composition by acidification with an acid or acids. A variety of inorganic and organic acids can be used for this purpose. Examples include organic acids such as citric acid and adipic acid while inorganic acid examples include phosphoric acid and hydrochloric acid. These acidified amine salts could also be formulated into the composition as supplied in the acid form from the manufacturer.

As noted previously, the ionic bond formed between the cationic colorant inhibitor and the anionic colorant leads to a hydrophobic coacervate upon neutralization of the charge in both species. Being hydrophobic, the solubility of the coacervate is very low in hydrophilic liquids such as urine. In addition, the solubility in urine is further limited due to the intermolecular forces between the coacervate and the carrier matrix and other components within the carrier matrix. For example, stearyl containing cationic quaternary ammonium salts can form the coacervate with the activated anionic bromocresol green. The stearyl groups within the coacervate interact through intermolecular binding forces with other stearyl moieties in the carrier matrix. For instance, the organic acids of monostearyl phosphate and monostearyl citrate would be expected to form intermolecular forces of attraction with the stearyl containing coacervate. In addition, stearyl alcohol and the alkyl groups of many waxes would also be be expected to form intermolecular forces of attraction with the stearyl containing coacervate.

Thus, coacervate formation is the preferred mode in inhibiting leaching of the colorant into the aqueous urine. But, it is not required for inhibiting leaching of the colorant. Compositions without cationic materials necessary to form the coacervate have also exhibited reduced leaching. As noted, this is due to intermolecular forces binding the activated anionic colorant within the carrier matrix. For example, hydrophobic regions within the molecular structure of the colorant can interact with both hydrophobic carrier matrix materials and components formulated into the carrier matrix.

The amount of colorant leaching was measured in systems where both ionic bonding lead to coacervate formation and where only intermolecular forces lead to inhibiting leaching. Ideally, the amount of colorant leaching is inhibited completely such that no colorant is detected in urine or other aqueous test solvents such as synthetic urine. In some embodiments, minimal colorant leaching is acceptable since the wetness indicator pattern is maintained with superior sharpness and color contrast. In addition, minimal colorant leaching does not lead to contamination of the diaper's topsheet. The amount of leaching in each of these compositions was measured by using the Leaching Value Test Methods described in detail below. For 20 minutes of exposure to the synthetic urine composition, the wetness indicators of the present invention preferably have a 20 Minute Leaching Value of less than 300 micrograms of colorant leached per gram of wetness indicator (see bar 90 in FIGS. 6 and 7 below) and most preferably less than 100 micrograms of colorant leached per gram of wetness indicator (see bar 92 in FIGS. 6 and 7 below) as measured via the 20 Minute Leaching Value Test Method described in detail below. The 20 Minute Leaching Value is defined as the micrograms of colorant leached per gram of wetness indicator during exposure to synthetic urine for twenty minutes. For 3 hours of exposure to the synthetic urine composition, the wetness indicators of the present invention have a 3 Hour Leaching Value of less than 600 micrograms of colorant leached per gram of wetness indicator (see bar 94 in FIGS.

6 and 7 below), preferably less than 300 micrograms of colorant leached per gram of wetness indicator (see bar 96 in FIGS. 6 and 7 below), and most preferably less than 100 micrograms of colorant leached per gram of wetness indicator (see bar 98 in FIGS. 6 and 7 below). The 3 Hour Leaching Value is defined as the micrograms of colorant leached per gram of wetness indicator after exposure to the synthetic urine for three hours. The details for the measurement for both the 20 Minute Leaching Value and the 3 Hour Leaching Value are given below in the sections describing the 20 Minute Leaching Value Test Method, the 1 Hour Leaching Value Test Method, the 3 Hour Leaching Value Test Method, and the 14 Hour Leaching Value Test Method.

20 Minute Leaching Value Test Method

The 20 Minute Leaching Value is measured using the following 20 Minute Leaching Value Test Method. Cut out a 38 mm diameter circular piece of diaper backsheet material using a circular die tool. A nonlimiting example of a backsheet material is microporous polyethylene with a basis weight of 37 grams per square meter as available from Tredegar Industries, Richmond, Va., U.S.A. Weigh this blank circular backsheet sample on an analytical balance accurate to at least four decimal places. Record this weight.

Heat and magnetically stir the wetness indicator formulation on a hot plate until it reaches a temperature of 95–100° C. Using a wooden tongue depressor or metal spatula, apply a thin coating of the molten urine indicator material onto the circular diaper backsheet material such that the total weight of the wetness indicator composition on the disk is between 0.03 g and 0.15 g. The entire surface of the backsheet sample should be covered with a substantially uniform film of the wetness indicator as judged by its visible appearance to the naked eye. Discard sample if the entire surface of the backsheet sample is not covered or if the film is substantially non-uniform. Weigh and record the total weight of each wetness indicator coated backsheet disk. Calculate and record the weight to the ten-thousandth place of the wetness indicator applied to each backsheet disk. Discard any samples that do not fall between 0.03 g and 0.15 g of total wetness indicator deposited onto the backsheet sample.

Using a nitrile gloved index finger cover, apply approximately 0.05 g to 0.15 g of a tacky microcrystalline wax (MULTIWAX™ W-835 or equivalent) at a temperature of 20° C. to the bottom of a 60 ml, 50 mm diameter glass sample jar. Spread the microcrystalline wax on the inside base of the jar so it encompasses an area approximately 12 mm in diameter in the center of the inside base of the jar.

Carefully place the wetness indicator coated backsheet disk onto the microcrystalline wax in the center of the inside base of the glass jar. The wetness indicator coated side should face up. Using a nitrile gloved index finger, carefully press the backsheet sample into the wax such that the sample sticks to the base of the jar.

Prepare a synthetic urine composition by weighing and dissolving the following ingredients in 5000.0 grams of distilled water:

TABLE 1

Composition of Synthetic Urine Composition

| Ingredient | Amount (grams) | Weight % in formula |
|---|---|---|
| Distilled water | 5000.0 | 99.43% |
| Sodium Sulfate. | 10.00 | 0.20% |
| Ammonium dihydrogenphosphate | 4.25 | 0.08% |
| Ammonium hydrogenphosphate | 0.75 | 0.01% |

TABLE 1-continued

Composition of Synthetic Urine Composition

| Ingredient | Amount (grams) | Weight % in formula |
|---|---|---|
| Calcium Chloride dihydrate | 1.25 | 0.02% |
| Magnesium Chloride hexahydrate | 2.50 | 0.05% |
| Pottasium Chloride | 10.00 | 0.20% |
| SUM | 5028.75 | 100.00% |

Heat and magnetically stir the synthetic urine composition on a hot plate until it reaches a temperature of 37–39° C. and the mixture is clear, transparent, and colorless with no signs of particulate matter. Keep covered to avoid evaporation of the water. Add 20.0 g of this heated synthetic urine to the sample jar containing the wetness indicator sample disk. Tightly seal the jar with its lid and shake up and down ten times. Shake with a frequency of approximately two cycles per second and an amplitude of approximately 25 cm. Allow the jar to sit at ambient conditions of approximately 20° C. and 1 bar for 20 minutes. For this 20 minute exposure time and all other exposure times, eight replicates for each unique wetness indicator composition should be tested using this 20 Minute Leaching Value Test Method.

After the test time interval has elapsed, shake the jar up and down an additional 5 times (same amplitude and frequency as noted previously) to uniformly distribute any leached colorant. Use a 5 ml disposable syringe to extract approximately 3–4 ml of liquid from the sample jar. Place a syringe filter (glass fiber, 1 micrometer pore size) on the syringe and filter the liquid into a 1 cm pathlength spectrophotometer cuvette.

Measure the absorbance of the sample at a wavelength of 616 run using a properly calibrated visible or UV-visible spectrophotometer. The spectrophotometer is calibrated by initially preparing a set of standards made by dissolving the acid form of bromocresol green into the synthetic urine described above. The standards should be made in the following concentrations by first weighing out exactly 0.100 g of the acid form of bromocresol green on an analytical balance accurate to three decimal places and dissolving the indicator in 2999.9 g of synthetic urine at room temperature to produce the most concentrated sample and then diluting the most concentrated sample by weight to produce the less concentrated samples. The standard concentrations are noted below:

TABLE 2

Composition of Colorant Standards for Instrument Calibration:

| | | |
|---|---|---|
| A | 3.33E–03% | Dissolve 0.100 g of colorant in 2999.9 g of Synthetic Urine |
| B | 1.67E–03% | Combine 10.00 g A with 10.00 g synthetic urine |
| C | 6.67E–04% | Combine 1.00 g A with 49.00 g synthetic urine |
| D | 3.33E–04% | Combine 1.00 g A with 9.00 g synthetic urine |
| E | 1.67E–04% | Combine 1.00 g B with 9.00 g synthetic urine |
| F | 6.67E–05% | Combine 1.00 g C with 9.00 g synthetic urine |
| G | 3.33E–05% | Combine 1.00 g D with 9.00 g synthetic urine |

A synthetic urine blank should also be included in the set of standards. Zero the absorbance of the spectrophotometer at 616 nm using the synthetic urine blank. Measure and record the absorbance for each of the bromocresol green standards and the synthetic urine blank. Plot the absorbance versus concentration and calculate the best fitting equation to the plotted data. Use this fitted calibration curve equation to calculate the concentration of the bromocresol green in the unknown diffusion samples.

From the calculated colorant concentration in each unknown, calculate the actual micrograms of colorant leached from the wetness indicator sample into the 20.0 g of synthetic urine at each time interval. Divide this calculated amount of colorant leached into the synthetic urine by the total gram weight of wetness indicator initially coated onto the blank diaper backsheet disk. Report and record this result as the Leaching Value in units of micrograms of colorant leached per gram of wetness indicator. The 20 Minute Leaching Value is defined as the micrograms of colorant leached per gram of wetness indicator during exposure to 20.0 grams of synthetic urine for 20 minutes.

1 Hour Leaching Value Test Method

The 1 Hour Leaching Value Test Method is identical to the 20 Minute Leaching Value Test Method except the prepared samples are exposed to 20.0 grams of the synthetic urine for a total time of 1 hour rather than 20 minutes. The 1 Hour Leaching Value is defined as the micrograms of colorant leached per gram of wetness indicator during exposure to 20.0 grams of synthetic urine for 1 hour.

3 Hour Leaching Value Test Method

The 3 Hour Leaching Value Test Method is identical to the 20 Minute Leaching Value Test Method except the prepared samples are exposed to 20.0 grams of the synthetic urine for a total time of 3 hours rather than 20 minutes. The 3 Hour Leaching Value is defined as the micrograms of colorant leached per gram of wetness indicator during exposure to 20.0 grams of synthetic urine for 3 hours.

14 Hour Leaching Value Test Method

The 14 Hour Leaching Value Test Method is identical to the 20 Minute Leaching Value Test Method except the prepared samples are exposed to 20.0 grams of the synthetic urine for a total time of 14 hours rather than 20 minutes. The 14 Hour Leaching Value is defined as the micrograms of colorant leached per gram of wetness indicator during exposure to 20.0 grams of synthetic urine for 14 hours.

The following Table 3 summarizes the Leaching Values measured at the four exposure times of 20 minutes, 1 hour, 3 hours, and 14 hours for three formulas that are examples of compositions of this invention and one commercially available hot melt wetness indication (HMWI) composition available from Bostik-Findley, Milwaukee, Wis., U.S.A. This commercially available HMWI is designated HMWI-1. Leaching Values for all four of the compositions listed in table 1 were measured by using the previously described Leaching Value Test Methods; thus, the samples within the row designation of 0.33 hrs were tested using the 20 Minute Leaching Value Test Method. The samples within the row designation of 1.00 hrs were tested using the 1 hour Leaching Value Test Method and so on. The means listed in columnar form for each composition were the arithmetic mean Leaching Values as calculated from eight replicates for each unique composition at each unique exposure time. Thus for example, the mean calculated for Formula 3 at 3 hours denotes a mean 3 Hour Leaching Value of 250 micrograms of pH indicator per gram of wetness indicator as calculated by taking the average of eight replicates.

The compositions designated in Table 3 as Formula 1, Formula 2, and Formula 3 were made according to the directions given below. It is clear from the tabulated results that the quaternary ammonium salt containing compositions of Formula 1 and Formula 2 are superior to both Formula 3 and the HMWI-1 in inhibiting leaching of the pH indicator (bromocresol green) at all synthetic urine exposure times. As noted previously, this is hypothesized to be due to the ionic chemical bond formed between the cationic quaternary ammonium salt and the activated anionic pH indicator. This coacervate inhibits leaching of the pH indicator due to its low solubility in the aqueous synthetic urine and its high solubility in the carrier matrix due to intermolecular binding forces.

It is also important to note that even though the non-quaternary containing Formula 3 listed below was inferior to the quaternary containing Formula 1 and 2, it was superior to the hot melt wetness indicator designated as HMWI-1. As noted, the inhibition of leaching in Formula 3 is due to intermolecular binding forces between the colorant and other components of the carrier matrix. Specifically for Formula 3, the wax, stearyl alcohol, C20-C40 Pareth-40, and the stearyl phosphate could also participate in intermolecular binding with the activated bromocresol green pH indicator.

TABLE 3

| | Micrograms of pH Indicator Leached per Gram of Wetness Indicator | | | |
|---|---|---|---|---|
| Time (hours) | Formula 1 (Mean) | Formula 2 (Mean) | Formula 3 (Mean) | HMWI-1 (Mean) |
| 0.33 | 33 | 39 | 77 | 370 |
| 1.0 | 57 | 68 | 130 | 320 |
| 3.0 | 59 | 41 | 250 | 800 |
| 14.0 | 93 | 120 | 430 | 710 |

Figure 6:
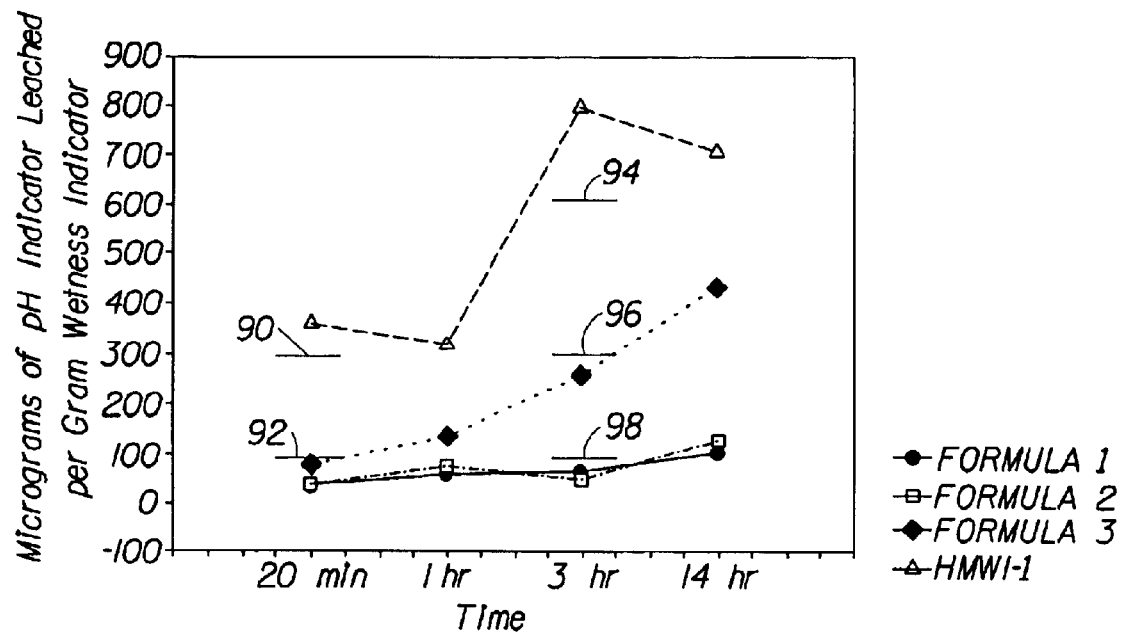
FIG. 6 shows a graph of pH indicator leaching at various exposure times.

FIG. 6 shows a graph with the Leaching Values as measured by the previously described procedures for four synthetic urine exposure times: 20 minutes, 1 hour, 3 hours, and 14 hours. The y-axis denotes the micrograms of pH indicator leached per gram of wetness indicator while the x-axis denotes the exposure time. The graph clearly shows the superiority of the cationic quaternary ammonium compound containing formulas 1 and 2 in inhibiting leaching of the colorant. In this case, the colorant is activated bromocresol green and the leaching inhibitor is a cationic quaternary ammonium salt. The superior leaching inhibition is due to the previously described coacervate formation and binding of this coacervate within the carrier matrix due to the previously described intermolecular forces. The detailed composition and recipe information is given below for each of the formulas 1 through 3. As noted, the non-quaternary containing formula 3 below also inhibits leaching more effectively than the HMWI (designated HMWI-1). This is due to the previously described intermolecular binding forces present in this Formula 3. The amount of leaching in each of these compositions was measured by using the Leaching Value Test Methods described previously. The bar 90 denoted in FIG. 6 notes the preferred 20 Minute Leaching Value of less than 300 micrograms of colorant leached per gram of wetness indicator and bar 92 denotes the most preferred 20 Minute Leaching Value of less than 100 micrograms of colorant leached per gram of wetness indicator as measured via the 20 Minute Leaching Value Test Method described previously. Bar 94 denotes the preferred 3 Hour Leaching Value of less than 600 micrograms of colorant leached per gram of wetness indicator, bar 96 denotes the more preferred 3 Hour Leaching Value of less than 300 micrograms of colorant leached per gram of wetness indicator, and bar 98 denotes the most preferred 3 Hour Leaching Value of less than 100 micrograms of colorant leached per gram of wetness indicator. All of the 3 Hour Leaching Values were measure using the 3 Hour Leaching Value Test Method as described previously.

Figure 7:
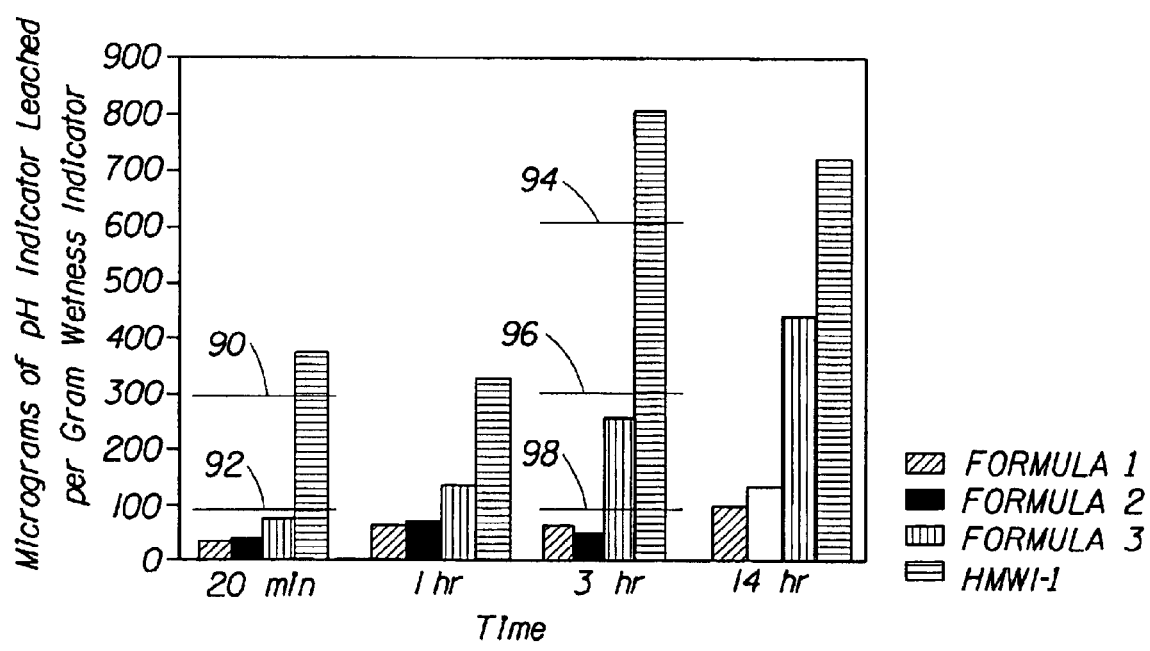
FIG. 7 shows a bar graph of pH indicator leaching at various exposure times.

FIG. 7 shows a bar graph with the Leaching Values as measured by the previously described Leaching Value Test Methods for four synthetic urine exposure times: 20 minutes, 1 hour, 3 hours, and 14 hours. The y-axis denotes the micrograms of pH indicator leached per gram of wetness indicator while the x-axis denotes the exposure time. The bar graph once again clearly shows the superiority of the cationic quaternary ammonium containing formulas 1 and 2 in inhibiting leaching of the colorant. In this case, the colorant is activated bromocresol green and the leaching inhibitor is a quaternary ammonium salt. The superior leaching inhibition is due to the previously described coacervate formation and binding of this coacervate within the carrier matrix due to the previously described intermolecular forces. The detailed composition and recipe information is given below for each of the formulas 1 through 3. As noted, the non-quaternary containing formula 3 also inhibits leaching more effectively than the HMWI (designated HMWI-1). This is due to the previously described intermolecular binding forces present in this Formula 3. The amount of leaching in each of these compositions was measured by using the Leaching Value Test Methods described previously. The bar 90 denoted in FIG. 7 notes the preferred 20 Minute Leaching Value of less than 300 micrograms of colorant leached per gram of wetness and bar 92 denotes the most preferred 20 Minute Leaching Value of less than 100 micrograms of colorant leached per gram of wetness indicator as measured via the 20 Minute Leaching Value Test Method described previously. Bar 94 notes the preferred 3 Hour Leaching Value of less than 600 micrograms of colorant leached per gram of wetness indicator, bar 96 notes the more preferred 3 Hour Leaching Value of less than 300 micrograms of colorant leached per gram of wetness indicator, and bar 98 notes the most preferred 3 Hour Leaching Value of less than 100 micrograms of colorant leached per gram of wetness indicator. All of the 3 Hour Leaching Values were measure using the 3 Hour Leaching Value Test Method as described previously.

Exemplary Embodiments

The unique blends having the following compositions exemplify the invention. The numbers for each formula are identical to the formula numbers described previously.

FORMULA 1:

| Function | Class | Chemical Name | Weight Percent |
|---|---|---|---|
| Carrier Matrix | Fatty Alcohol | Stearyl Alcohol | 49.8% |
| Carrier Matrix | Wax | Microcrystalline Wax | 10.0% |
| Acid | Organic Acid | Stearyl Phoshate (acid form) | 10.0% |
| Leaching Inhibitor | Quaternary Ammonium compound | Dimethyl(2-ethyl-hexylhydrogenated tallowalkyl)ammonium methyl sulfate | 10.0% |
| Colorant | pH Indicator | Bromocresol Green (acid form) | 0.2% |
| Surfactant | Nonionic Type | C20–C40 Pareth-40 | 20.0% |

The preceding Formula 1 is made by first weighing out the correct amounts of stearyl alcohol, microcrystalline wax, and stearyl phosphate into a stainless steel container. The stearyl alcohol should be a white waxy solid with a purity of at least 97% and such a stearyl alcohol may have no more than 2% of arachidyl alcohol, and may possess a melt point of 56–60° C. The product designated CO1897 stearyl alcohol available from The Procter & Gamble Company of Cincinnati, Ohio, U.S.A. is a current example of an acceptable material. The microcrystalline wax should be a high molecular weight petroleum based wax consisting of saturated branched and cyclic non-polar hydrocarbons and such a wax may have a melting point in the range of 60–95° C. The product designated MULTIWAX™ W-835 available from the Crompton Corporation of Petrolia, Pa., U.S.A. is a good example of a microcrystalline wax meeting these requirements. Arlatone™ MAP180 is a good example of stearyl phosphate as available from Uniqema Incorporated in Wilmington, Del., U.S.A. Heat and mix this mixture at 100–110° C. until this mixture is clear, transparent and colorless. Add the correct amount of the dimethyl(2-ethylhexylhydrogenated tallowalkyl)ammonium methyl sulfate to the stearyl alcohol premix and heat at 100–110° C. for 10 minutes. The dimethyl(2-ethylhexylhydrogenated tallowalkyl)ammonium methyl sulfate may have a quaternary salt content of 81.5–84.5%, may possess a free amine and free amine salt impurity content of no more than 4%, and may possess an HLB of 17–18. The product designated ARQUAD™ HTL8(W)-MS available from Akzo-Nobel of Chicago, Ill., U.S.A. is a good example of a dialkyldimethyl quaternary ammonium salt currently meeting these requirements. To this mixture, add the correct amount of the powdered acid form of bromocresol green (as available from the Aldrich Chemical Company, Milwaukee, Wis., U.S.A.). Heat and mix at 100–110° C. for 20 mixtures. Finally, to this mixture, add the correct amount of C20-C40 Pareth-40 which has been preheated to a temperature of 110–110° C. Such a C20-C40 Pareth-40 may have a molecular weight ($M_n$) between 2200 and 2400, an ethylene oxide content between 75–85%, an HLB of approximately 16, and a melting point between 80–94° C. The product designated PERFORMATHOX™ 480 available from New Phase Technologies of Sugar Land, Tex., U.S.A is a good example of a C20-C40 Pareth-40 meeting these requirements. Mix the entire composition at 100–110° C. until it is clear, transparent and yellow-orange in color. Dispense into appropriate containers and allow to cool to room temperature.

FORMULA 2:

| Function | Class | Chemical Name | Weight Percent |
|---|---|---|---|
| Carrier Matrix | Fatty Alcohol | Stearyl Alcohol | 41.78% |
| Carrier Matrix | Wax | Microcrystalline Wax | 8.42% |
| Surfactant | Nonionic Type | C20–C40 Pareth-40 | 19.64% |
| Acid | Organic Acid | Stearyl Phoshate (acid form) | 9.82% |
| Colorant | pH Indicator | Bromocresol Green (acid form) | 0.20% |
| Leaching Inhibitor | Quaternary Ammonium compound | Dimethyl(2-ethyl-hexylhydrogenated tallowalkyl)ammonium methyl sulfate | 10.12% |
| Viscosity Increasing Agent | Modified Clay | Quaternium-18 Hectorite | 10.02% |

The preceding Formula 2 is made by first weighing out the correct amounts of stearyl alcohol, microcrystalline wax, dimethyl(2-ethylhexylhydrogenated tallowalkyl)ammonium methyl sulfate, and quaternium-18 hectorite. The stearyl alcohol should be a white waxy solid with a purity of at least 97 % and such a stearyl alcohol may have no more than 2% of arachidyl alcohol, and may possess a melt point of 56–60° C. The product designated CO1897 stearyl alcohol available from The Procter & Gamble Company of Cincinnati, Ohio, U.S.A. is a current example of an acceptable material. The microcrystalline wax should be a high molecular weight petroleum based wax consisting of saturated branched and cyclic non-polar hydrocarbons and such a wax may have a melting point in the range of 60–95° C. The product designated MULTIWAX™ W-835 available from the Crompton Corporation of Petrolia, Pa., U.S.A. is a good example of a microcrystalline wax meeting these requirements. The dimethyl(2-ethylhexylhydrogenated tallowalkyl)ammonium methyl sulfate may have a quaternary ammonium salt content of 81.5–84.5%, may possess a free amine and free amine salt impurity content of no more than 4%, and may possess an HLB of 17–18. The product designated ARQUAD™ HTL8(W)-MS available from Akzo-Nobel of Chicago, Ill., U.S.A. is a good example of a dialkyldimethyl quaternary ammonium salt currently meeting these requirements. BENTONE GEL™ MIO is a good example of quaternium-18 hectorite as available from Rheox Incorporated, Hightstown, N.J., U.S.A. Heat this mixture to 90° C. and mix with a prop mixer for 15 minutes. Next, shear this mixture with a laboratory shear mixer set to 16,000 RPM for 15 minutes. In a separate container, weigh out the correct amounts of C20-C40 Pareth-40, the acid form of stearyl phosphate, and the acid form of bromocresol green (as available from the Aldrich Chemical Company, Milwaukee, Wis., U.S.A.) and heat and mix at 100° C. until this second mixture is clear, transparent and orange in color. Such a C20-C40 Pareth-40 may have a molecular weight ($M_n$) between 2200 and 2400, an ethylene oxide content between 75–85%, an HLB of approximately 16, and a melting point between 80–94° C. The product designated PERFORMATHOX™ 480 available from the Crompton Corporation of Petrolia, Pa., U.S.A. is a good example of a C20-C40 Pareth-40 meeting these requirements. Arlatone™ MAP180 is a good example of stearyl phosphate as available from Uniqema Incorporated in Wilmington, Del., U.S.A. After shearing the first mixture, add the correct amount of the heated (90–100° C.) second mixture and prop mix for 15 minutes until the entire composition is opaque, homogeneous, and orange in color. Dispense into appropriate containers and allow to cool to room temperature.

FORMULA 3:

| Function | Class | Chemical Name | Weight Percent |
| --- | --- | --- | --- |
| Carrier Matrix | Fatty Alcohol | Stearyl Alcohol | 39.60% |
| Carrier Matrix | Wax | Microcrystalline Wax | 39.60% |
| Surfactant | Nonionic Type | C20–C40 Pareth-40 | 20.0% |
| Acid | Organic Acid | Stearyl Phoshate (acid form) | 0.60% |
| Colorant | pH Indicator | Bromocresol Green (acid form) | 0.20% |

The preceding Formula 3 is made by first weighing out the correct amounts of stearyl alcohol, and microcrystalline wax into a stainless steel container. The stearyl alcohol should be a white waxy solid with a purity of at least 97% and such a stearyl alcohol may have no more than 2% of arachidyl alcohol, and may possess a melt point of 56–60° C. The product designated CO1897 stearyl alcohol available from The Procter & Gamble Company of Cincinnati, Ohio, U.S.A. is a current example of an acceptable material. The microcrystalline wax should be a high molecular weight petroleum based wax consisting of saturated branched and cyclic non-polar hydrocarbons and such a wax may have a melting point in the range of 60–95° C. The product designated MULTIWAX™ W-835 available from the Crompton Corporation of Petrolia, Pa., U.S.A. is a good example of a microcrystalline wax meeting these requirements. Heat and mix at 90–100° C. until this mixture of stearyl alcohol and microcrystalline wax is clear, transparent and colorless. In a separate container, weigh out the correct amounts of C20-C40 pareth-40, the acid form of stearyl phoshate, and the acid form of bromocresol green (as available from the Aldrich Chemical Company, Milwaukee, Wis., U.S.A.). Arlatone™ MAP180 is a good example of stearyl phosphate as available from Uniqema Incorporated in Wilmington, Del., U.S.A. Such a C20-C40 Pareth-40 may have a molecular weight ($M_n$) between 2200 and 2400, an ethylene oxide content between 75–85%, an HLB of approximately 16, and a melting point between 80–94° C. The product designated PERFORMATHOX™ 480 as available from New Phase Technologies of Sugar Land, Tex., U.S.A is a good example of a C20-C40 Pareth-40 meeting these requirements. Heat this second mixture to a temperature of 100–110° C. and mix until it is clear, transparent and orange in color. Next, slowly add the contents of this second mixture to first mixture containing the stearyl alcohol and microcrystalline wax. Heat to 90–100° C. and mix until the entire mixture is clear, transparent and orange in color. Dispense into appropriate containers and allow to cool to room temperature.

The wetness indicator may be applied to a substrate via any means of liquid or semi-liquid application as known in the art, including, but not limited to, slot coating, spraying, gravure printing, ink jet printing, and digital printing. Alternatively, the wetness indicator may be a solid or semi-solid material affixed to a substrate via adhesive bonding, chemical bonding or intermolecular force bonding. Multiple indicators may be applied to the same substrate in overlapping or nonoverlapping geometries. The solidification process may be accelerated via the use of convective mass transport, if evaporation of a solvent is required, or convective or conductive heat transfer, e.g., cooling via air or chilled rolls, etc.

The substrate to which the wetness indicator is applied or otherwise affixed may comprise any one, or a combination, of the structural components of the article, including the backsheet, topsheet, fasteners, absorbent material, etc., or may be a separate element added or applied to the product. The substrate may be a film, nonwoven, woven, or foam material and may comprise synthetic and/or natural materials.

The indicator preferably provides a signal visible from outside the product while the product is being worn. Preferably, the signal, i.e., color or contrast change, is visible through the backsheet or garment-facing covering of the article. The signal preferably is visible within a short time after urination. Generally, the signal should be visible within about 15 minutes after urine contacts the indicator. Preferably, the signal is visible within about 5 minutes after contact with urine. In certain embodiments, the absorbent system of the article may be designed to allow urine to contact the indicator in certain regions of the product at various loading levels. For example, the absorbent system may be designed to allow urine to contact the wetness indicator in the crotch region of the product on the first urination, but contact the wetness indicator in other regions of the product only after the amount of urine in the product reaches a predetermined threshold value. For example, the absorbent core may have limited ability to distribute urine from a given region of the article until it contains sufficient urine to activate a wetness indicator in this region, thereby preventing activation of the wetness indicator in adjacent regions of the article until the overall urine loading in the article increases above a given level. As the total urine loading in the article increases, more regions of the articles will contain sufficient urine to activate wetness indicators that may be located in those regions.

The wetness indicator may comprise two or more colorants, each having different activating criteria, i.e., different $pK_a$ values, a pH and an enzyme trigger, etc., colors, or other properties. The wetness indicating compositions may be applied in any pattern or in conjunction with permanent graphics on the outer surfaces of a wearable article, as disclosed in U.S. Pat. No. 4,022,211 issued to Timmons, which is herein incorporated by reference. The varying colors, triggers, etc., may facilitate interactive scenes, sequences, or displays providing information regarding relative fullness/wetness of the article or merely provide entertainment and/or aesthetic value. For example, the wetness indicating composition may contain one colorant that turns blue and another that turns red upon contact with urine. Alternatively, one portion of the graphic may appear and another portion may disappear upon contact with urine.

The wetness indicating compositions of the present invention may be adapted to detect the presence of residual feces on the skin of a wearer. The pH of feces typically ranges from about pH 5 to about pH 8. Once exposed to the air, fecal pH increases by about 0.5 pH unit every 30 minutes. Thus, compositions having pH transition values of about 7–8 may reliably detect the presence of residual fecal contamination at least about 1–2 hours old. Incorporation of these fecal contamination-indicating compositions onto a wearer-contacting surface, such as the topsheet, of a wearable article facilitates the transfer of the composition to the wearer's skin. The presence of fecal contamination, i.e., high pH material, on the skin causes the colorant to activate and display a signal to the caregiver indicating the need for additional or more through cleaning of the skin, particularly in the area where the presence of residual fecal material is indicated. The advantage of this embodiment is the resultant reduced possibility of the colorant penetrating the wearer's skin versus the application/transfer of the colorant alone to the skin. Penetration of the colorant in this example is inhibited due to the binding of the colorant to components of the wetness indicating composition that are too large to effectively diffuse into the skin.

What is claimed is:

1. A wetness indicating composition comprising a colorant disposed in a carrier matrix, the carrier matrix comprising a leaching inhibitor, the colorant providing a visible signal when activated by urine and resisting leaching from the carrier matrix by being chemically bound to the leaching inhibitor.

2. The wetness indicating composition of claim 1 wherein the colorant is a pH indicator.

3. The wetness indicating composition of claim 1 wherein the leaching inhibitor comprises a cationic species.

4. The wetness indicating composition of claim 3 wherein the cationic species is a quaternary ammonium compound.

5. The wetness indicating composition of claim 3 wherein the cationic species is a cationic clay compound.

6. The wetness indicating composition of claim 1 wherein the carrier matrix comprises a microcrystalline wax.

7. The wetness indicating composition of claim 1 wherein the carrier matrix comprises a surfactant.

8. The wetness indicating composition of claim 1 wherein the colorant is ionically or covalently bound to the leaching inhibitor.

9. The wetness indicating composition of claim 1 having a colorant Leaching Value of no more than 300 micrograms of colorant leached per gram of the wetness indicator as measured by a 3 Hour Leaching Value Test Method as disclosed herein.

10. The wetness indicating composition of claim 1 wherein the carrier matrix comprises a $C_{12}$–$C_{50}$ linear primary alcohol.

11. The wetness indicating composition of claim 1 wherein the carrier matrix comprises an organic acid.

12. The wetness indicating composition of claim 1 wherein the carrier matrix comprises a viscosity increasing agent.

13. A wetness indicating composition comprising a colorant disposed in a carrier matrix, the carrier matrix comprising a leaching inhibitor, the colorant providing a visible signal when activated by urine and resisting leaching from the carrier matrix by being intermolecularly bound to the leaching inhibitor.

14. A disposable absorbent article comprising a wetness indicating composition affixed to a structural component of the article, the wetness indicating composition comprising a colorant disposed in a carrier matrix, the carrier matrix comprising a leaching inhibitor, the colorant providing a visible signal when activated by urine and resisting leaching from the carrier matrix by being chemically or intermolecularly bound to the leaching inhibitor.

15. The disposable absorbent article of claim 14 wherein the colorant is a pH indicator.

16. The disposable absorbent article of claim 14 wherein the colorant is ionically or covalently bound to the leaching inhibitor.

17. The disposable absorbent article of claim 14 wherein the wetness indicating composition has a colorant Leaching Value of no more than about 300 micrograms of colorant leached per gram of the wetness indicator as measured by a 20 Minute Leaching Value Test Method as disclosed herein.

18. The disposable absorbent article of claim 14 wherein the wetness indicating composition has a colorant Leaching Value of no more than about 600 micrograms of colorant leached per gram of the wetness indicator as measured by a 3 Hour Leaching Value Test Method as disclosed herein.

19. The disposable absorbent article of claim 14 wherein the wetness indicating composition has a colorant Leaching Value of no more than about 300 micrograms of colorant leached per gram of the wetness indicator as measured by a 3 Hour Leaching Value Test Method as disclosed herein.

20. The disposable absorbent article of claim 14 wherein the wetness indicating composition has a colorant Leaching Value of no more than about 100 micrograms of colorant leached per gram of the wetness indicator as measured by a 3 Hour Leaching Value Test Method as disclosed herein.

* * * * *

UNITED STATES PATENT AND TRADEMARK OFFICE
CERTIFICATE OF CORRECTION

PATENT NO. : 6,772,708 B2
DATED : August 10, 2004
INVENTOR(S) : Thomas James Klofta et al.

It is certified that error appears in the above-identified patent and that said Letters Patent is hereby corrected as shown below:

Title page,
Delete Item "[63] Related U.S. Application Data, Continuation of application No. 10/015,818 filed on October 30, 2001, now Pat. No. 6,655,781."

Column 1,
Delete lines 4, 5, 6, "This is a continuation of application Ser. No.. 10/015,618 filed on Oct. 30, 2001, now U.S. Pat. No. 6,655,781 which is hereby incorporated by reference herein."

Signed and Sealed this

Seventh Day of December, 2004

JON W. DUDAS
*Director of the United States Patent and Trademark Office*